(12) United States Patent
Kelly et al.

(10) Patent No.: US 7,389,699 B2
(45) Date of Patent: Jun. 24, 2008

(54) METHOD AND APPARATUS FOR TESTING SHEAR STRENGTH OF CURVED CORE MATERIAL

(75) Inventors: John M. Kelly, Wildwood, MO (US);
Derek A. Hebda, O'Fallon, MO (US);
Susan K. Graf, St. Louis, MO (US);
Arthur N. Leaf, St. Charles, MO (US);
Harvey J. Tomko, St. Peters, MO (US)

(73) Assignee: The Boeing Company, Chicago, IL (US)

( * ) Notice: Subject to any disclaimer, the term of this patent is extended or adjusted under 35 U.S.C. 154(b) by 75 days.

(21) Appl. No.: 11/250,333

(22) Filed: Oct. 13, 2005

(65) Prior Publication Data
US 2007/0084296 A1 Apr. 19, 2007

(51) Int. Cl.
*G01M 5/00* (2006.01)
*G01N 3/24* (2006.01)

(52) U.S. Cl. .................... 73/843; 73/802; 73/856

(58) Field of Classification Search ............. 73/802, 73/826–830, 834–835, 838, 841–851, 856–859; 702/43; G01N 3/24; G01L 5/00
See application file for complete search history.

(56) References Cited

U.S. PATENT DOCUMENTS

| | | | | |
|---|---|---|---|---|
| 4,875,376 A | * | 10/1989 | Fischer | .................... 73/852 |
| 5,280,730 A | * | 1/1994 | Peres et al. | ................ 73/846 |
| 5,540,972 A | * | 7/1996 | Jaegers et al. | ............... 428/116 |
| 5,616,848 A | * | 4/1997 | Hemingway et al. | .......... 73/838 |
| 6,055,867 A | * | 5/2000 | Dunne et al. | ................. 73/849 |
| 6,880,409 B2 | * | 4/2005 | Kawabe et al. | ................ 73/856 |
| 7,155,982 B2 | * | 1/2007 | Oesmann et al. | ............. 73/841 |
| 2004/0069072 A1 | * | 4/2004 | Kawabe et al. | ................ 73/841 |
| 2006/0134408 A1 | * | 6/2006 | Kaneko | ...................... 428/343 |

OTHER PUBLICATIONS

Information Disclosure Statement filed on Mar. 3, 2008.*

* cited by examiner

*Primary Examiner*—Edward Lefkowitz
*Assistant Examiner*—Jonathan Dunlap
(74) *Attorney, Agent, or Firm*—Ostrager Chong Flaherty & Broitman P.C.

(57) ABSTRACT

A method and an apparatus for testing the shear strength of curved core material. The method comprises the steps of: (a) bonding one side of a test specimen of curved core material to a convex curved surface of a first support; (b) bonding the other side of the test specimen to a concave curved surface of a second support; (c) mounting the first support so that it is pivotable about a pivot axis; (d) fixing the second support to a rigid frame; (e) after step (a) through (d) have been performed, causing the first support to pivot about the pivot axis; and (f) during step (e), continuously monitoring a parameter that will manifest a change if and when shear induced in the test specimen causes a structural change indicative of failure of the test specimen. A linearly displaceable head is mechanically coupled to the first support in a manner such that linear displacement of the head is converted into pivoting of the first support. The monitored parameter is the load produced as the test specimen resists pivoting of the first support.

19 Claims, 6 Drawing Sheets

METHOD AND APPARATUS FOR TESTING SHEAR STRENGTH OF CURVED CORE MATERIAL

BACKGROUND OF THE INVENTION

This invention generally relates to techniques for measuring properties of structural materials. In particular, the invention relates to techniques for measuring properties of curved structural materials, such as curved core material.

Sandwich panels are widely used in the aerospace industry and other industries where strong, lightweight structures are required. Such a sandwich panel typically includes a lightweight central core structure that is sandwiched between two composite or metal face sheets. The face sheets are adhesively bonded to opposite sides of the core. Reinforcing cores are often necessary in large panels to provide sufficient rigidity and structural strength in the panel so that the panel can withstand substantial loading.

Various core structures are presently in use, with the two main types being rigid foam and honeycomb. For structures having rigid foam cores, the face sheets contact the foam over a relatively large surface area, which ensures a strong bond. For structures having honeycomb cores, the surface area which is available for bonding to the face sheets is much smaller than the available surface area for foam cores. The honeycomb cells extend transversely between the face sheets so that the only surfaces available for bonding to the face sheets are the outer edges of the cells.

A typical sandwich panel has a bottom composite or metallic layer manufactured from a fibrous material that is impregnated with a resin. A core material of amorphous foam or honeycomb structure is then positioned on the bottom layer. A top composite or metallic layer is then bonded to the core. An edge layer is then applied to connect the top and bottom layers and to seal the core therebetween. This assembly is then cured in an autoclave or an oven with a vacuum bag at elevated temperatures and pressures.

The reinforcing core is typically designed to have substantial compression resistance along a core axis. The core is typically oriented with respect to the top and bottom layers so that the core axis is perpendicular thereto. In this way, the structural panel undergoes loading in a fashion similar to a beam wherein the top and bottom layers correspond to the flange portions of a beam and the core corresponds to the web portion of a beam. The core itself has little resistance to compression in a direction perpendicular to the core axis.

Various techniques are known for forming curved structural panels of the foregoing type. The curved core material can be subjected to substantial shearing forces when the curved structural panel undergoes substantial loading. Accordingly, the curved core material must be designed to have sufficient shear strength to withstand the shearing forces produced by such loading. The need to validate the shear strength of curved core material is of increasing importance due to its increasing use in airframe structures. Some existing testing methodologies use flat core material and analytical techniques to determine allowable shear strength properties for structure containing curved core material.

There is a need for an effective mechanical test method for directly measuring the shear strength of curved core materials in order to validate analytical techniques or develop design allowables. Such a test method would facilitate improved structural design and could also be used as a screening method to evaluate potential curved core materials in the proposed use state.

BRIEF DESCRIPTION OF THE INVENTION

The invention is directed to a methodology for determining the shear strength of curved core materials. The invention is also directed to an apparatus for determining the shear strength of curved core materials.

One aspect of the invention is a method of testing the shear strength of curved core material, comprising the following steps: (a) inducing shear in a test specimen of curved core material; and (b) continuously monitoring a parameter that will manifest a change if and when the induced shear causes a structural change indicative of failure of the test specimen.

Another aspect of the invention is a method of testing the shear strength of curved core material, comprising the following steps: (a) bonding one side of a test specimen of curved core material to a convex curved surface of a first support; (b) bonding the other side of the test specimen to a concave curved surface of a second support; (c) mounting the first support so that it is pivotable about a pivot axis; (d) fixing the second support to a rigid frame; (e) after step (a) through (d) have been performed, causing the first support to pivot about the pivot axis; and (f) during step (e), continuously monitoring a parameter that will manifest a change if and when shear induced in the test specimen causes a structural change indicative of failure of the test specimen.

A further aspect of the invention is an apparatus for testing the shear strength of curved core material, comprising: a support frame; a shaft pivotably mounted to the support frame, the shaft being pivotable about a pivot axis; a first support fixed to the shaft and having a convex curved surface; a second support fixed to the support frame and having a concave curved surface, and a test specimen of curved core material having one side bonded to the convex curved surface of the first support and another side bonded to the concave curved surface of the second support.

Other aspects of the invention are disclosed and claimed below.

DETAILED DESCRIPTION OF THE INVENTION

Figure 1:
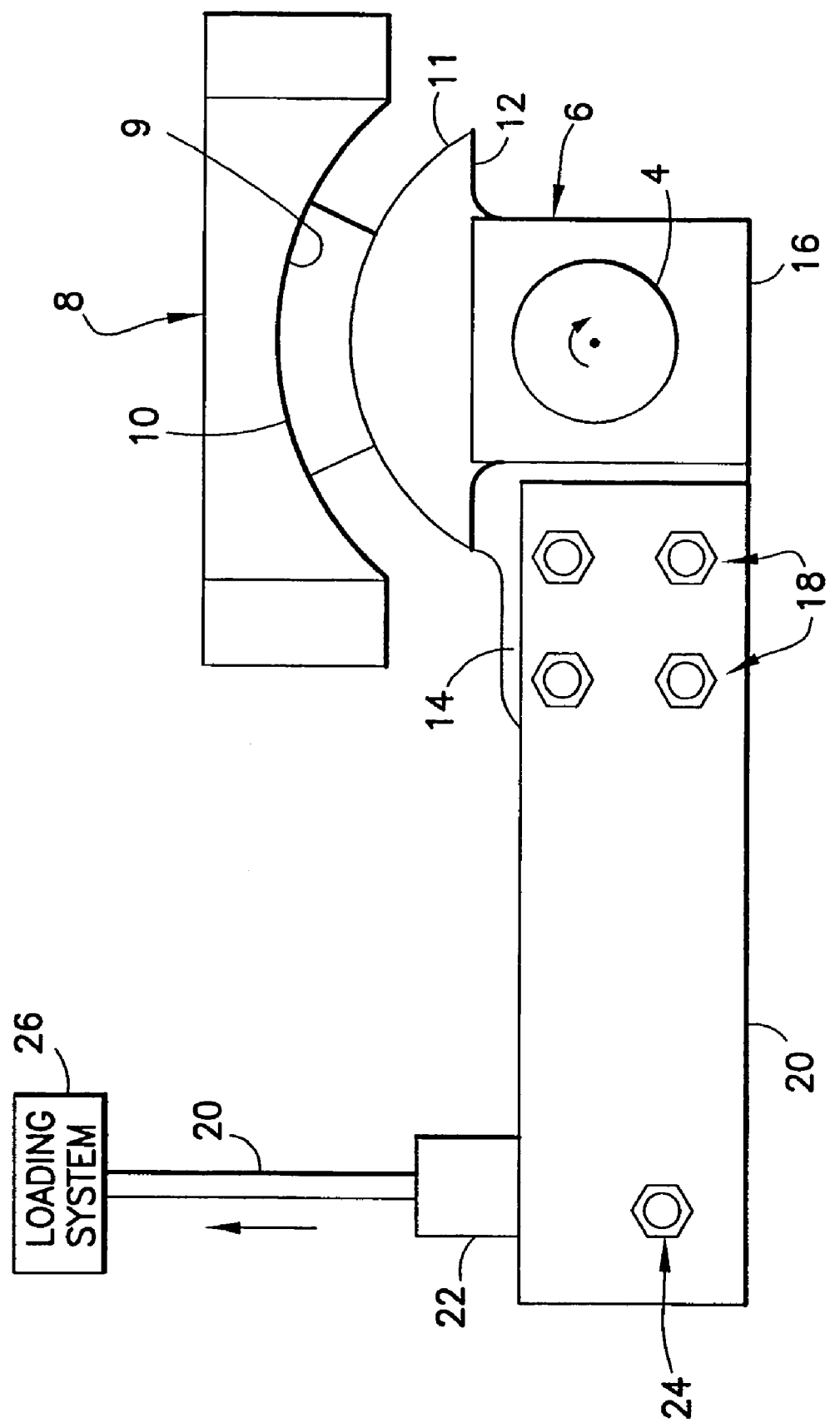
FIG. 1 is a drawing showing a side view of portions of a test fixture assembly for mechanically determining the shear strength of a curved core material in accordance with one embodiment of the invention.

A method for testing the shear strength of curved core material In accordance with one embodiment of the invention will now be disclosed with reference to FIG. 1. A test specimen 10 comprises curved core material, such as amorphous foam or a honeycomb structure. The thickness or height of the curved core material is preferably substantially constant. The test specimen 10 is bonded to a test fixture, as is schematically represented in FIG. 1. The test specimen 10, when viewed from one end, as seen in FIG. 1, has the shape of an arc, with the rest of the core material extending into the page. The various components of the test fixture (described in detail below), including the portions to which the test specimen was bonded, were made of steel.

One side of the test specimen 10 of curved core material is bonded to a convex curved surface 11 of a support 6 that is fixed to a shaft 4. The ends of the shaft 4 are rotatably mounted in respective fixed bearings (not shown in FIG. 1), thereby forming a pivotable support assembly. The bearings are fixed to a support frame (not shown in FIG. 1). The support frame is a rigid structure that is fixed to a table or other rigid base of the testing machine (not shown). The convex curved surface 11 of the support 6 has a radius of curvature that is substantially centered at the axis of shaft 4.

Figure 2:
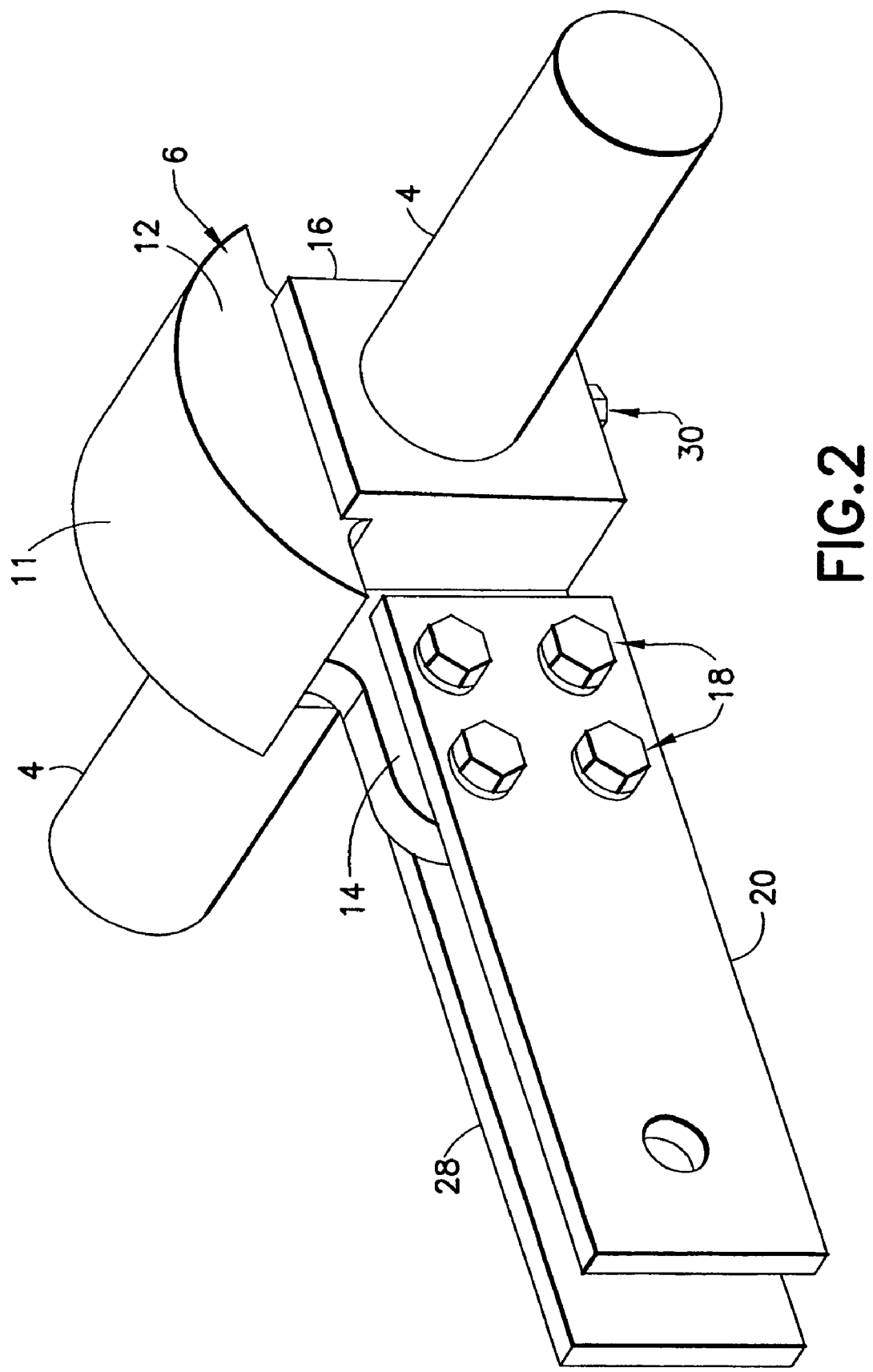
FIG. 2 is a drawing showing an isometric view of a rotatable subassembly that forms part of the assembly depicted in FIG. 1.
Figure 3:
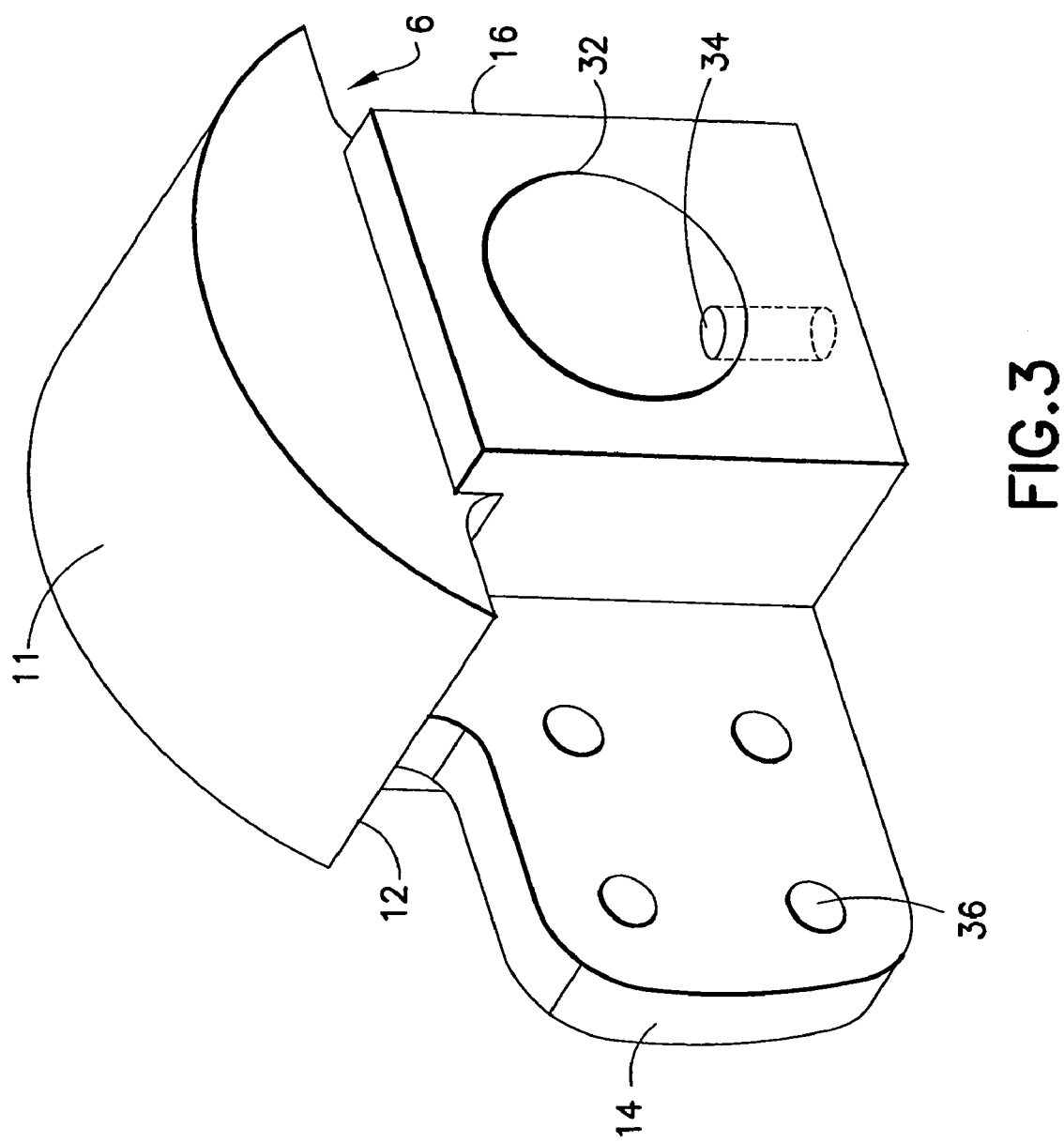
FIG. 3 is a drawing showing an isometric view of a support that is a component of the subassembly depicted in FIG. 2.

As best seen in FIG. 2, the support 6 comprises a support block 12 having a convex curved surface 11 in the shape of a section of a circular cylinder, a mounting block 16 that is fastened to an intermediate portion of the shaft 4, and a flange 14 that extends substantially perpendicular to the axis of the shaft 4 and has a thickness substantially less than the thickness of blocks 12 and 16. In one implementation, the support block 12, flange 14 and mounting block 16 are integrally formed as one monolithic structure. However, they could be separate parts welded or fastened together. As seen in FIG. 3, the mounting block 16 has a circular bore 32 having a radius slightly greater than the radius of the shaft. FIG. 2 shows the shaft 4 and support 6 in an assembled state, with an intermediate portion of the shaft residing inside the circular bore in the mounting block 16 and with the ends of the shaft 4 exposed on opposite sides of the support 6. The ends of the shaft will be rotatably seated in the aforementioned bearings.

Although only one unthreaded bore 34 is shown in FIG. 3, the bottom portion of the mounting block 16 of support 6 has three such unthreaded bores for the passage of respective bolts (e.g., the head of one of the bolts 30 can be seen in FIG. 2) that fasten the support 6 to the shaft 4. For this purpose, the shaft is provided with three threaded bores (not shown), to which the bolts 30 are threadably coupled during assembly.

Returning to FIG. 1, the other side of the test specimen 10 of curved core material is bonded to a concave curved surface 9 of a fitting 8 that is fixed to the aforementioned support frame, e.g., by means of clamps (not shown). The concave curved surface 9 of the fitting 8 has a radius of curvature that is greater than the radius of the convex curved surface 11 of support block 12 by an amount substantially equal to the thickness of the test specimen 10. Ideally the radius of curvature of the concave curved surface 9 of the fitting 8 is also substantially centered at the axis of shaft 4, but this will depend on the final position of the fitting 8 after it has been bonded to the test specimen 10. For instance, if, during bonding of the fitting 8 to the test specimen 10, the position of the fitting 8 shifts slightly while the adhesive is curing, the fitting will not contact the support frame squarely. Shims wedged between the fitting 8 and the support frame can be employed to account for such variability if necessary to ensure that the core material is placed in a state of pure shear rather than adding a small twisting force on it.

Figure 4:
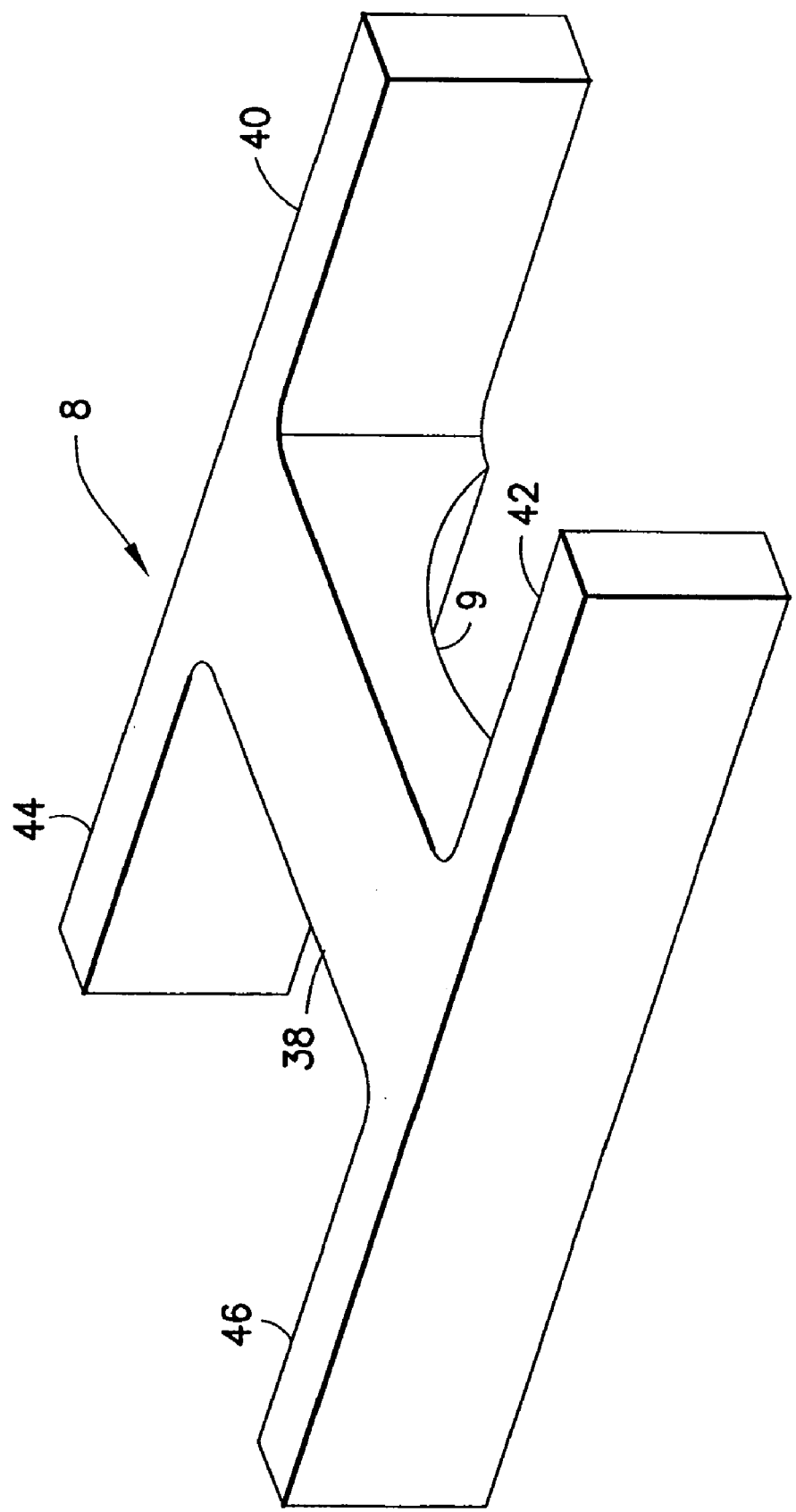
FIG. 4 is a drawing showing an isometric view of a fitting that is a component of the assembly depicted in FIG. 1.

The shape of the fitting 8 in accordance with one embodiment of the invention is shown in detail in FIG. 4. The fitting 8 comprises a central member 38, the bottom surface of which comprises the aforementioned concave curved surface 9, integrally formed with four fingers 40, 42, 44 and 46, by means of which the fitting 8 can be clamped to the support frame.

Referring again to FIG. 2, a pair of lever arms 20 and 28, each in the form of a rectangular plate, are fastened at one end thereof to the flange 14 of support 6 by means of four fastener assemblies 18, each fastener assembly comprising a nut and a bolt. The bolts pass through respective holes formed in one end of the arms 20, 28 and respective holes 36 (see FIG. 3) formed in the flange 14. As shown in FIG. 2, the lever arms 20 and 28 are disposed substantially perpendicular to the axis of shaft 4.

Referring to FIG. 1, the other ends of the lever arms (only lever arm 20 is visible in FIG. 1) have respective holes for receiving a bolt of a fastener assembly 24 that couples the lever arms to a loading system 26 of the testing machine by way of a rod 20 and a head 22. The head 22 is pivotably coupled to the bolt that passes through the distal ends of the lever arms. During each test, the head 22 is displaced upward at a constant head travel rate by the loading system 26. The loading system used for one test program was a 60-kip load system commercially available from Satec Systems Inc., Model No. 60CG. As the head displaces upward, the distal ends of the lever arms are also displaced upward, which causes the rigid subassembly comprising the lever arms 20 and 28 (see FIG. 2), support 6 and shaft 4 to pivot about the axis of shaft 4.

Referring again to FIG. 1, pivoting of the support 6 induces shear in the test specimen 10. As the head 22 moves, the support frame supporting the fitting 10 does not move. The force from the head 22 trying to move the distal ends of the lever arms upward is reacted through the test specimen to the support frame. Shear is induced as the test specimen (the top of which is bonded to the stationary fitting) resists pivoting of the support block 12.

Figure 5:
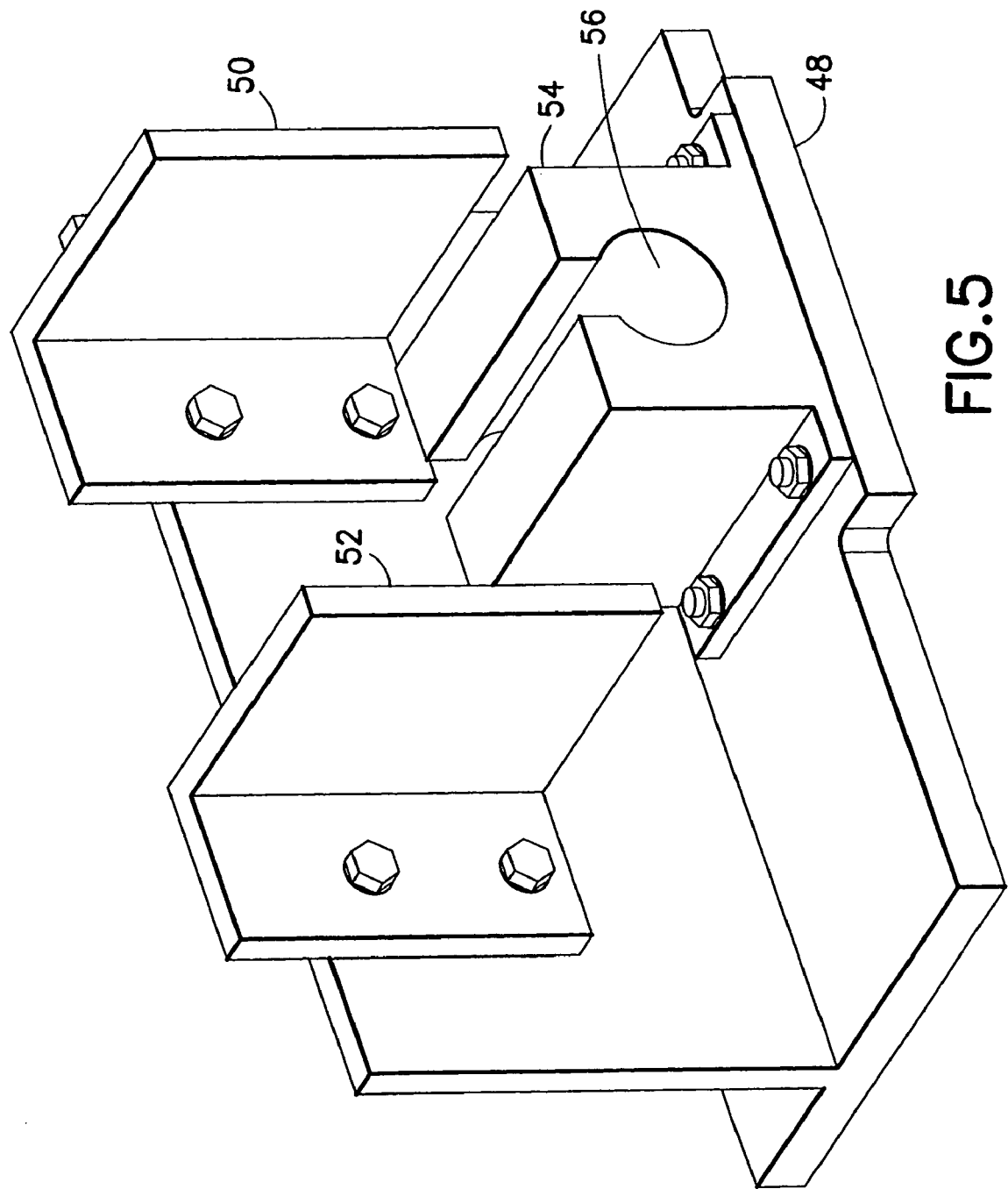
FIG. 5 is a drawing showing an isometric view of a support frame that rotatably supports the subassembly depicted in FIG. 2 and fixedly supports the fitting depicted in FIG. 4.

One half of a support frame in accordance with one embodiment of the invention is shown in FIG. 5. Each half of the support frame comprises an inverted T-shaped member 48, a pair of angled members 50 and 52 fastened to the stem of the inverted T-shaped member 48, and a bearing 54 fastened to the base of the inverted T-shaped member 48. The inverted T-shaped member 48 is in turn fastened or clamped to the aforementioned table or base of the testing machine. One end of shaft 4 (see FIG. 1) is inserted into the circular channel 56 of bearing 54, thereby supporting the shaft for rotation.

In accordance with one implementation, the support frame was partially disassembled every time a new specimen was put in for testing. In the partially disassembled state, one half of the support frame (as seen in FIG. 5) is fastened or clamped to the testing machine table, while the other half is not. The shaft and lever arms were bolted to the lower support (after the lower and upper supports have been bonded to the test specimen). The shaft was then slid axially into the bearing that remained clamped to the testing machine. Then the other half of the support frame (a mirror image of the structure shown in FIG. 5) was reassembled by sliding its bearing onto the other end of the shaft and then clamping it down to the testing frame.

A test program was undertaken using test specimens comprising curved honeycomb core material. Thirty 0.9-inch-thick Fiberglass Flex-core HRP/F50-5.5 honeycomb core samples were provided for use in this test program. One half of these specimens had a nominal radius of 3 inches and the other half had a nominal radius of 5 inches. Thirteen additional 0.9-inch-thick Nomex Flex-core HRH-10/F50-5.5 honeycomb core samples, having a nominal radius of 3 inches, were also provided. Samples to be tested in the dry condition were dried in an oven at a temperature of 250° F. for 72 hours. Samples to be tested in the wet condition were dried in an oven at a temperature of 250° F. for 120 hours. Five specimens of each type were tested in the wet condition. Specimens to be tested in the wet condition were subjected to a 190° F./95% relative humidity environment for 43 days followed by a 190° F./85% relative humidity environment for 16 days.

Test specimens were bonded to the loading fixture using EA9394 paste adhesive. Specimens tested in the dried condition were placed in an oven at a temperature of 150° F. for 1 hour after being bonded to the support block and fitting of the test fixture and then allowed to cure overnight at room temperature. Specimens tested in the wet condition were allowed to cure a minimum of three days at room temperature prior to testing. Specimens tested at other than ambient conditions were heated or cooled to the desired test temperature and maintained at the test temperature for 10 minutes prior to loading. Test specimens were loaded via the test fixture to induce shear into the honeycomb core specimens. A typical curved core shear test setup is presented in FIG. 1. Due to the nature of the test fixture geometry and the desire to have loading rates similar to standard core shear methods, the 3-inch-radius specimens were loaded using a head travel rate of 0.064 inch per minute and the 5-inch-radius test specimens were loaded using a head travel rate of 0.040 inch per minute. Those head travel rates were determined to match the testing rates specified in ASTM-C-273 for flat core specimens of 0.50 mm/minute. Load versus head travel was continuously monitored during loading.

Figure 6:
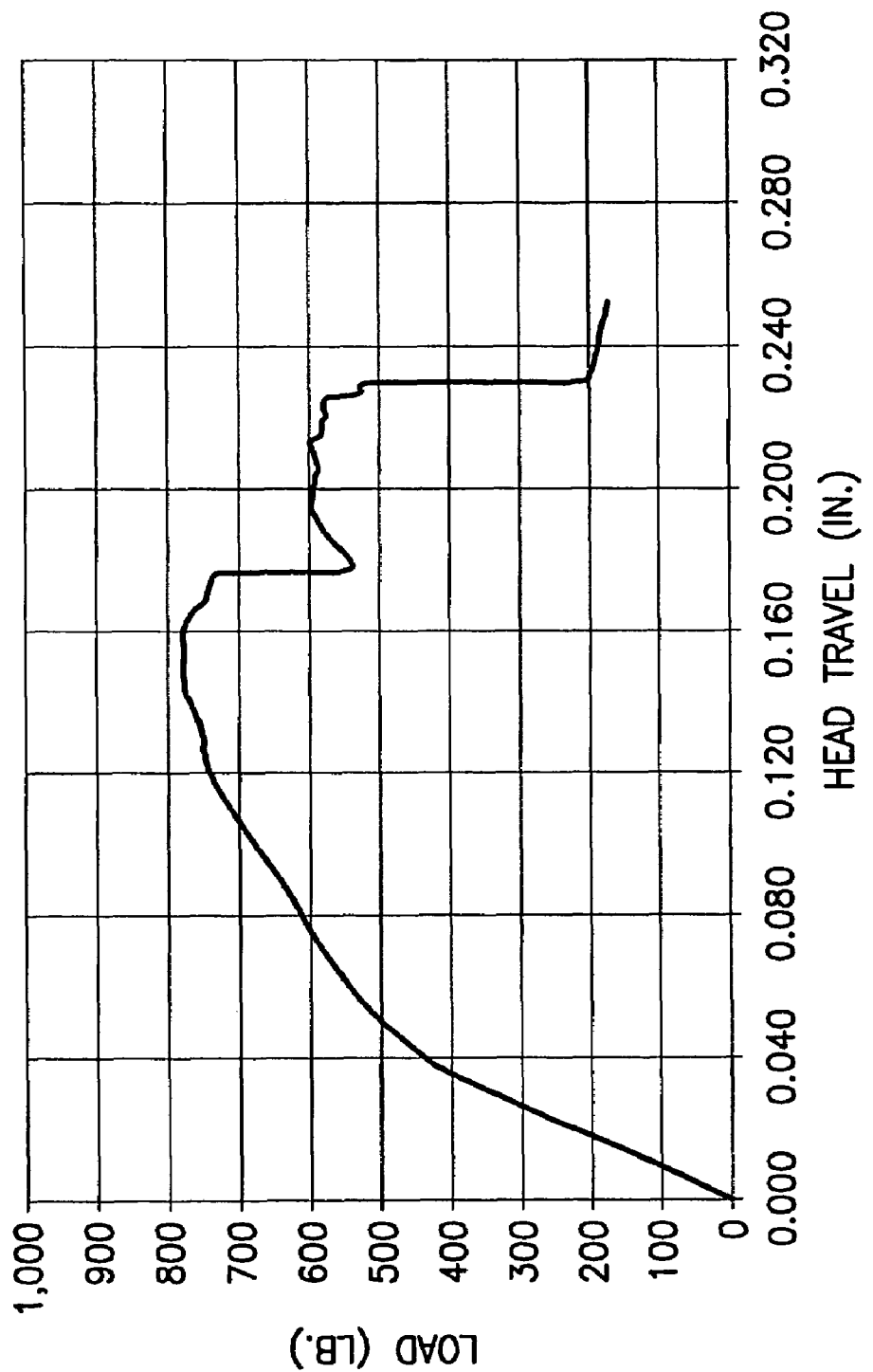
FIG. 6 is a graph of load versus head travel for a typical curved core shear test.

A plot of load versus head travel for a typical curved core shear test is presented in FIG. 6. The sudden decreases in the detected load correspond to structural changes indicative of either failure of the test specimen (i.e., core shear failure mode) or failure of the adhesive bonding between the test specimen and one of the supports (i.e., adhesive failure mode).

All specimens displayed some mode of failure of core shear. Most specimens tested in the dry condition had only core shear as the mode of failure. All specimens tested in the wet condition had a mixed mode of failure, undergoing core shear and some degree of adhesive failure between the loading blocks and the adhesive. For specimens having a mixed mode of failure, an analysis concluded that first the core failed, which induced a peeling stress in the adhesive, causing the adhesive to separate from the cylindrical surface. A small number of specimens tested in the dry condition had a predominant mode of failure between the loading blocks and the adhesive.

It is recommended that steps be taken to prevent the adhesive from disbanding from the cylindrical steel surfaces of the pivotable support and the fitting. To increase the strength of the adhesive bonds, the steel surfaces can be prepared by applying a bond primer before the specimens are bonded.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

In the absence of explicit language in any method claim setting forth the order in which certain steps should be performed, the method claims should not be construed to require that recited steps be performed in the order in which they are recited.

The invention claimed is:

1. A method of testing the shear strength of curved core material, comprising the following steps:
    preparing a convex curved surface of a first support by applying bond primer thereto;
    preparing a concave curved surface of a second support by applying bond primer thereto;
    bonding one side of a test specimen of curved core material to the bond-primed convex curved surface of the first support and the other side of the test specimen to the bond-primed concave curved surface of the second support;
    inducing shear in the test specimen by causing the first support to move relative to the second support; and
    continuously monitoring a parameter that will manifest a change if and when the induced shear causes a structural change indicative of failure of the test specimen.

2. The method as recited in claim 1, further comprising the steps of mounting the first support so that it is pivotable about a pivot axis and fixing the second support, wherein said causing step comprises the step of causing the first support to pivot about the pivot axis.

3. The method as recited in claim 2, further comprising the step of mechanically coupling a head to the first support in a manner such that linear displacement of the head is converted into pivoting of the first support, wherein said causing step comprises linearly displacing the head at a constant rate.

4. The method as recited in claim 1, further comprising the step of drying the test specimen in an oven before steps (a) and (b).

5. The method as recited in claim 4, further comprising the step of exposing the test specimen to humidity after the drying step and before steps (a) and (b).

6. The method as recited in claim 1, wherein the curved core material has a honeycomb structure.

7. The method as recited in claim 1, wherein the curved core material is amorphous foam.

8. The method as recited in claim 3, wherein the parameter is the load produced as the test specimen resists pivoting of the first support.

9. A method of testing the shear strength of curved core material, comprising the following steps:
    (a) preparing a convex curved surface of a first support by applying bond primer thereto;
    (b) preparing a concave curved surface of a second support by applying bond primer thereto;
    (c) bonding one side of a test specimen of curved core material to the bond-primed convex curved surface of the first support;
    (d) bonding the other side of the test specimen to the bond-primed concave curved surface of the second support;
    (e) mounting the first support so that it is pivotable about a pivot axis;
    (f) fixing the second support to a rigid frame;
    (g) after steps (a) through (f) have been performed, causing the first support to pivot about the pivot axis; and
    (h) during step (g), continuously monitoring a parameter that will manifest a change if and when shear induced in the test specimen causes a structural change indicative of failure of the test specimen.

10. The method as recited in claim 9, further comprising the step of mechanically coupling a linearly displaceable head to the first support in a manner such that linear displacement of the head is converted into pivoting of the first support, wherein step (g) comprises linearly displacing the head at a constant rate.

11. The method as recited in claim 9, wherein the curved core material has a honeycomb structure.

12. The method as recited in claim 9, wherein the curved core material is amorphous foam.

13. The method as recited in claim 10, wherein the parameter is the load produced as the test specimen resists pivoting of the first support.

14. An apparatus for testing the shear strength of curved core material, comprising:
- a support frame;
- a shaft pivotably mounted to said support frame, said shaft being pivotable about a pivot axis;
- a first support fixed to said shaft and having a convex curved surface having bond primer applied thereon;
- a second support fixed to said support frame and having a concave curved surface having bond primer applied thereon, and
- a test specimen of curved core material having one side bonded to said bond-primed convex curved surface of said first support and another side bonded to said bond-primed concave curved surface of said second support.

15. The apparatus as recited in claim 14, wherein the curved core material has a honeycomb structure, each cell of the honeycomb having an axis that is substantially normal to said convex curved surface of said first support.

16. The apparatus as recited in claim 14, wherein said convex curved surface of said first support has a first radius approximately centered at said pivot axis of said shaft, while said concave curved surface of said second support has a second radius greater than said first radius.

17. The apparatus as recited in claim 14, wherein said convex curved surface of said first support has a cross-sectional shape that is constant in a direction parallel to said pivot axis, the cross section being taken in a plane perpendicular to said pivot axis.

18. The apparatus as recited in claim 14, further comprising an arm having one end rigidly coupled or connected to said first support, said arm having a longitudinal axis that is substantially orthogonal to said pivot axis.

19. The apparatus as recited in claim 18, further comprising a loading system coupled to the other end of said arm.

* * * * *